(12) United States Patent
Dantus (10) Patent No.: US 12,019,011 B2
(45) Date of Patent: Jun. 25, 2024

(54) LASER SYSTEM FOR BLOOD OR TISSUE ASSESSMENT

(71) Applicant: Board of Trustees of Michigan State University, East Lansing, MI (US)

(72) Inventor: Marcos Dantus, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 733 days.

(21) Appl. No.: 17/271,269

(22) PCT Filed: Aug. 29, 2019

(86) PCT No.: PCT/US2019/048848
§ 371 (c)(1),
(2) Date: Feb. 25, 2021

(87) PCT Pub. No.: WO2020/047279
PCT Pub. Date: Mar. 5, 2020

(65) Prior Publication Data
US 2021/0255148 A1    Aug. 19, 2021

Related U.S. Application Data

(60) Provisional application No. 62/725,521, filed on Aug. 31, 2018.

(51) Int. Cl.
*G01N 21/17* (2006.01)
*A61B 5/15* (2006.01)
(Continued)

(52) U.S. Cl.
CPC ... *G01N 21/1702* (2013.01); *A61B 5/150366* (2013.01); *G01N 21/45* (2013.01);
(Continued)

(58) Field of Classification Search
CPC .. G01N 21/1702; G01N 21/45; G01N 29/226; G01N 26/2418;
(Continued)

(56) References Cited

U.S. PATENT DOCUMENTS

| 6,405,069 B1 | 6/2002 | Oraevsky et al. |
| 2008/0014574 A1 | 1/2008 | Viator et al. |

(Continued)

FOREIGN PATENT DOCUMENTS

| CA | 2843445 A1 * | 2/2013 | ......... G01B 11/0675 |
| JP | 2004506893 A * | 3/2004 | ............. G01N 21/45 |
| JP | 2015507182 A * | 3/2015 | ............... C12Q 1/04 |

OTHER PUBLICATIONS

Kolkman, Roy G. M., et al., "In vivo photoacoustic imaging of blood vessels with a pulsed laser diode," Lasers Med Sci (2006) 21: 134-139.

(Continued)

*Primary Examiner* — John E Breene
*Assistant Examiner* — Rose M Miller
(74) *Attorney, Agent, or Firm* — Harness, Dickey & Pierce, PLC (57) ABSTRACT

A laser system for blood assessment is provided. Another aspect of a laser system includes a container within which is blood, a laser operable to emit a laser beam at the container to vibrate the blood, a detector operable to detect a vibrational characteristic of the blood, a controller connected to the detector operable to automatically determine a characteristic of the blood based at least in part on the vibrational characteristic detected by the detector, and a display operable to indicate a determination result from the controller. Another aspect of the present blood or tissue assessment laser system includes a laser, a power supply, a detector, a
(Continued)

controller and an electronic display, all contained within or coupled to a handheld and portable housing.

25 Claims, 6 Drawing Sheets

(51) Int. Cl.
*G01N 21/45* (2006.01)
*G01N 29/22* (2006.01)
*G01N 29/24* (2006.01)
*G01N 33/49* (2006.01)

(52) U.S. Cl.
CPC ....... *G01N 29/226* (2013.01); *G01N 29/2418* (2013.01); *G01N 33/49* (2013.01); *G01N 2291/02466* (2013.01); *G01N 2291/02475* (2013.01)

(58) Field of Classification Search
CPC .......... G01N 2291/02466; G01N 2291/02475; G01N 33/49; A61B 5/150366
USPC ......................................................... 73/655
See application file for complete search history.

(56) References Cited

U.S. PATENT DOCUMENTS

| | | |
|---|---|---|
| 2008/0289427 A1 | 11/2008 | Brandt et al. |
| 2013/0144148 A1 | 6/2013 | Li et al. |
| 2015/0282716 A1 | 10/2015 | Smeltzer et al. |
| 2016/0113507 A1 | 4/2016 | Reza et al. |
| 2017/0071475 A1 | 3/2017 | Irisawa |
| 2018/0146303 A1 | 5/2018 | Campbell et al. |

OTHER PUBLICATIONS

Bok, Tae-Hoon, et al., "Simultaneous assessment of red blood cell aggregation and oxygen saturation under pulsatile flow using high-frequency photoacoustics," Biomedical Optics Express, (Jul. 1, 2016) vol. 7, No. 7.

Strohm, Eric M., "Probing Red Blood Cell Morphology Using High-Frequency Photoacoustics," (2013) Biophysical Society.

Hysi, Eno, et al., "On the use of photoacoustics to detect red blood cell aggregation," Biomedical Optics Express, vol. 3, No. 9, 2326 (Sep. 1, 2012).

Saha, Ratan K., et al., "A simulation study on photoacoustic signals from red blood cells," Journal Acoustical Soc. Am. 129 (5) (May 2011).

Saha, Ratan K., et al. "Computational Investigation on the Photoacoustics of Malaria Infected Red Blood Cells," Plos One, (Dec. 2012) vol. 7, Issue 12, e51774.

Hysi, Eno, et al., "Photoacoustic ultrasound spectroscopy for assessing red blood cell aggregation and oxygenation," Journal of Biomedical Optics, 17 (12), 125006 (Dec. 2012).

Saytashev, Ilyas, et al., "Multiphoton excited hemoglobin fluorescence and third harmonic generation for non-invasive microscopy of stored blood," Biomedical Optics Express 3449, vol. 7, No. 9 (Sep. 2016).

Kibria, F., et al., "Identification of Red Blood Cell Rouleaux Formation Using Photoacoustic Ultrasound Spectroscopy," Proc. Of SPIE, vol. 8943 (894367-1) (2014).

* cited by examiner

LASER SYSTEM FOR BLOOD OR TISSUE ASSESSMENT

CROSS-REFERENCE TO RELATED APPLICATIONS

This application is a National Phase entry of PCT International Application No. PCT/US2019/048848, filed on Aug. 29, 2019, which claims priority to U.S. Provisional Patent Application Ser. No. 62/725,521, filed Aug. 31, 2018. The entire disclosure of the above applications are incorporated by reference herein.

BACKGROUND AND SUMMARY

This disclosure relates generally to a laser device and more particularly to a laser system for blood or tissue assessment.

It is known to use photoacoustic ultrasound spectroscopy and microscopy for blood imaging using high energy and/or ultrafast lasers. Examples of such experiments are disclosed in: F. Kibria et al., "Identification of Red Blood Cell Rouleaux Formation Using Photoacoustic Ultrasound Spectroscopy," Proc. of SPIE, Vol. 8943 (894367-1) (2014); and I. Saytashev, M. Dantus et al., "Multiphoton Excited Hemoglobin Fluorescence and Third Harmonic Generation for Non-Invasive Microscopy of Stored Blood," Biomed. Opt. Express, Vol. 7, No. 9 (Sep. 1, 2016 at 3449). These prior devices, however, employ expensive lasers which are not portable, as they rely on microscopic imaging.

Blood is a living organ. Thus, there is a need to assess the health of stored blood in a non-invasive, quick, safe, and chemical-free manner without breaching the storage container or bag. It is also desired to perform this blood assessment in an inexpensive and portable manner without the need for trained technicians. Blood has a limited storage or shelf life which must be assessed. However, this is made difficult by donor variability (for example, male/female and health status), as well as "storage lesion" effects. In fact, there are no devices in present use that can determine actual blood health noninvasively. Therefore, conventional protocols require blood to be discarded after 42 days regardless of health status. This approach is overly cautious in cases when the blood is still healthy and places patients at risk when the blood is no longer healthy. The present laser system solves all of these traditional concerns based on making actual assessments for each bag of blood in a very fast and easy to use manner.

Furthermore, it is typically difficult to differentiate between normal and cancerous tissue during surgery. Time consuming laboratory procedures have been traditionally used which may require multiple surgical procedures and/or overly-aggressive tissue removal during surgery. The present laser system, however, can provide an inexpensive and easy to use device which can provide essentially real-time results during the surgery.

In accordance with the present invention, a laser system for blood assessment is provided. Another aspect of a laser system includes a bag within which is blood, a laser operable to emit a laser beam at the container to vibrate the blood, a detector operable to detect a vibrational characteristic of the blood, a controller connected to the detector operable to automatically determine a characteristic of the blood based at least in part on the acoustic characteristic detected by the detector, and a display operable to indicate a determination result from the controller. Another aspect of the present blood or tissue assessment laser system includes a laser, a power supply, a detector, a controller and an electronic display, all contained within or coupled to a handheld and portable housing. A further aspect provides a laser system for assessing a characteristic of blood within a container based on vibrational characteristics of the blood due to ultrasonic vibration or acoustic shock due to emission of a laser beam, without the use of microscopy and without the use of imaging. A method of assessing an expiration, quality, bacteria or viral characteristic of a bag of blood, or cancerous tissue characteristic, based on laser-induced vibrational or acoustic shock characteristics in a portable machine, without the use of microscopy and without the use of imaging, is also disclosed.

The present laser system is advantageous over conventional devices since the present laser system is much less expensive and is portable. This allows the present laser system to be used in a vehicle, such as an ambulance or at an accident site in addition to allowing ease of transportation and use within a hospital or laboratory. Furthermore, the present laser system is able to use an inexpensive laser since microscopy and imaging are not needed. Additional advantages and features of the present laser system and method will become apparent from the following description and appended claims, taken in conjunction with the accompanying drawings.

DETAILED DESCRIPTION

Referring to FIGS. 1-4, a laser system and apparatus 21 are used for assessing blood 23 within a container such as a flexible polymeric bag 25. System 21 includes a portable and handheld housing 31 having a laterally elongated handle segment 33 and a somewhat perpendicularly and longitudinally elongated extension segment 35 which has a distal end 37 contacting against an exterior surface of container 25. A hand 39 of a person using the apparatus grips around an outside of handle segment 33 which is preferably cylindrical or may have an irregular arcuate surface to conform closer to the person's palm and fingers.

A power supply 41, such as a rechargeable battery, is located within an end of handle segment 33 and supplies electricity to a laser 43 also located within handle segment 33. Electrical terminals may protrude through an end of handle segment 33 to removeably mate the battery to an electrical charging station.

Laser 43 is preferably a pulsed diode laser emitting at least one laser light pulse having a wave length greater than 400 nm and a duration shorter than 100 ns, and more preferably a duration less than 3 ns. Furthermore, laser 43 has a visible frequency between 450-600 nm and more preferably between 530-570 nm. Laser 45 emits a continuous beam of light of about 0.5 mW total power and a wavelength between 650-850 nm. Such a laser can be obtained from OSRAM.

An optional second ns-pulsed diode laser (not shown) may also be located within housing 31. When both photodiode lasers 43 are employed, a wave length of about 500 nm is used for one of the lasers and a wave length of about 540-570 nm is used for the other of the lasers. This dual wave length configuration advantageously provides automated assessment of hemoglobin and meth-hemoglobin, without imaging.

A push button, rocking or sliding trigger switch 47 protrudes from handle segment 33 for movement by hand 39 to activate or deactivate electricity going to laser 43. Alternately or additionally, a container-contacting switch can be provided at distal end 37. Furthermore, a focusing lens 49 is located between laser 43 and a dichroic beam splitter 51. Additionally, an optical wedge 53 is located between beam splitter 51 and distal end 37. Lens 49, beam splitter 51 and wedge 53 are all optic members retained internal to the portable housing via brackets or polymeric molded walls of the housing.

An optoacoustic detector 71 is also located within handle segment 33 of housing 31. Detector 71 preferably acts as a Fizeau interferometer, with a negative lens 73 located between detector 71 and a polarizing beam splitter 55. A CW diode laser 45 is located within housing 31, longitudinally aligned with a centerline axis of extension segment 35 extending through beam splitter 51 and wedge 53. Laser 45 works with detector 71 to create the desired interferometry based on the acoustic vibrations reflected back from blood cells 23 in the laser light pulses or beam initially emitted from laser 43. Detector 71 is preferably a small silicon photodiode with an optical opening diameter of about 100 microns to function as a pinhole. An exemplary avalanche photodiode detector can be obtained from Marktech Optoelectronics Inc. as product No. MTAPD-06.

Diode laser 43 is a narrow bandwidth laser that emits coherent light pulses at blood cells 23. The collective acoustic vibrations of the blood cells are detected by interferometry and without imaging. Optical wedge 53 causes vertical interference fringes on the sensing beam from laser diode 45 that are virtually mapped onto a surface of bag 25 and motion of the fringes is sensed as vibrations. The optical area of detector 71 is smaller than a distance between the fringes so that the detector can detect this fringe motion. Moreover, negative lens 73 is employed to expand the fringes in order to improve the ability of detector 71 to detect or sense the spacing between the fringes. It is noteworthy that only the motion of the fringes is detected rather than imaging all of the fringes themselves.

Beam splitter 55 and a quarter-wave plate 57 are longitudinally aligned with and located between CW diode laser 45 and wedge 53. Additionally, a dark and non-reflective dump 92 is provided.

One or more printed circuit boards 91 and associated electrical circuits are also disposed with housing 31. The circuit boards include a microprocessor 93, a digital signal processing chip 95, a RAM and/or ROM memory chip 97, and a capacitor 99. Moreover, an electronic display 101 is coupled to and movable with housing 31. Display 101 employs an LED or LCD screen that provides numerical values, differing green or red colors, and/or other such graphical user interface indicia representing the determined and calculated results regarding the blood characteristics for the user to observe. Alternately, analog displays or lights may be connected to the electrical circuits.

Figure 8:
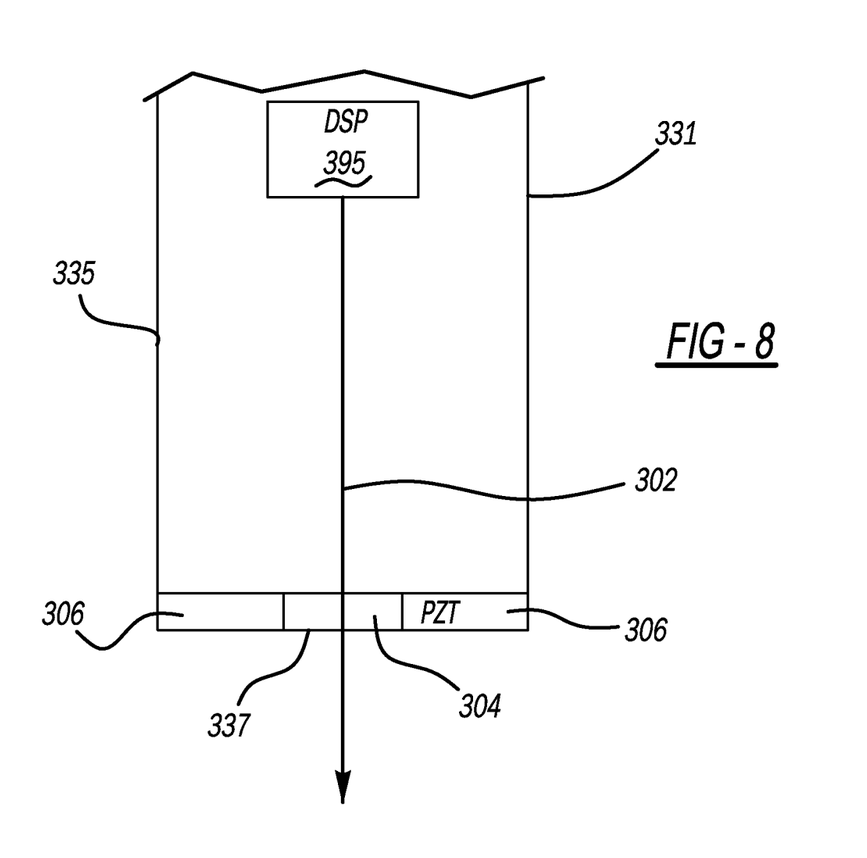
FIG. 8 is a diagrammatic side view showing an alternate configuration of the present laser system.

FIG. 8 illustrates a different embodiment of a portable and handheld laser system for blood assessment. A housing 331 includes a digital signal processing ("DSP") chip 395 within an extension segment 335 to amplify and magnify an area of interest, such as localized blood cells or tissue cells. A laser light pulse or beam 302 is emitted through a transparent window 304 at a distal end 337 of extension segment 335. Piezoelectric transducers ("PZT") 306 are also coupled to housing 331 adjacent distal end 337. The digital signal processing chip collects the reflective light and transmits it to electrical circuitry discussed hereinabove for assessment and display. This PZT approach does not require a CW laser, beam splitter, negative lens or wedge, and is therefore considerably less expensive than the prior embodiment.

Figure 1:
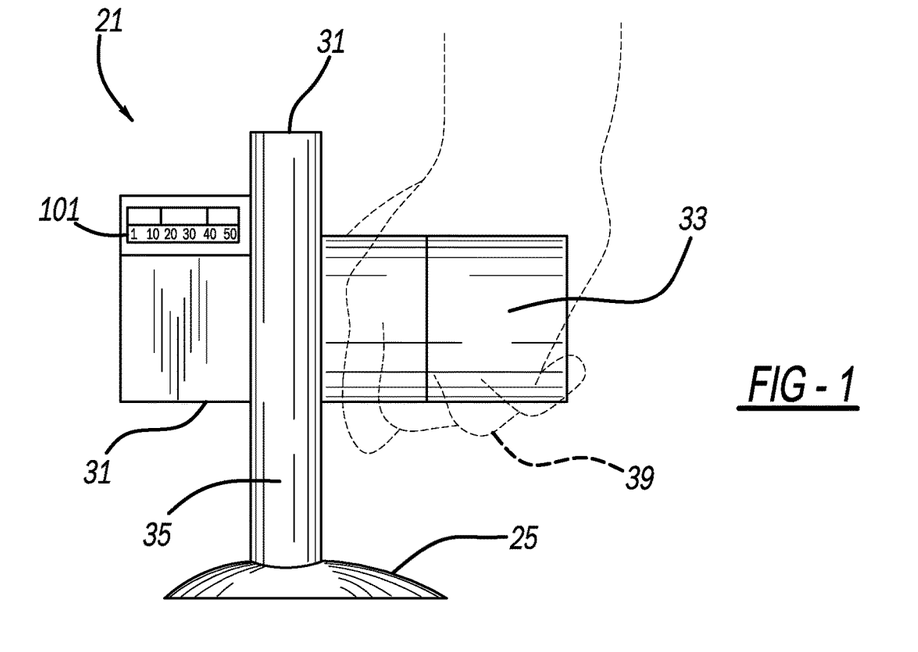
FIG. 1 is a side elevational view showing the present laser system.
Figure 2:
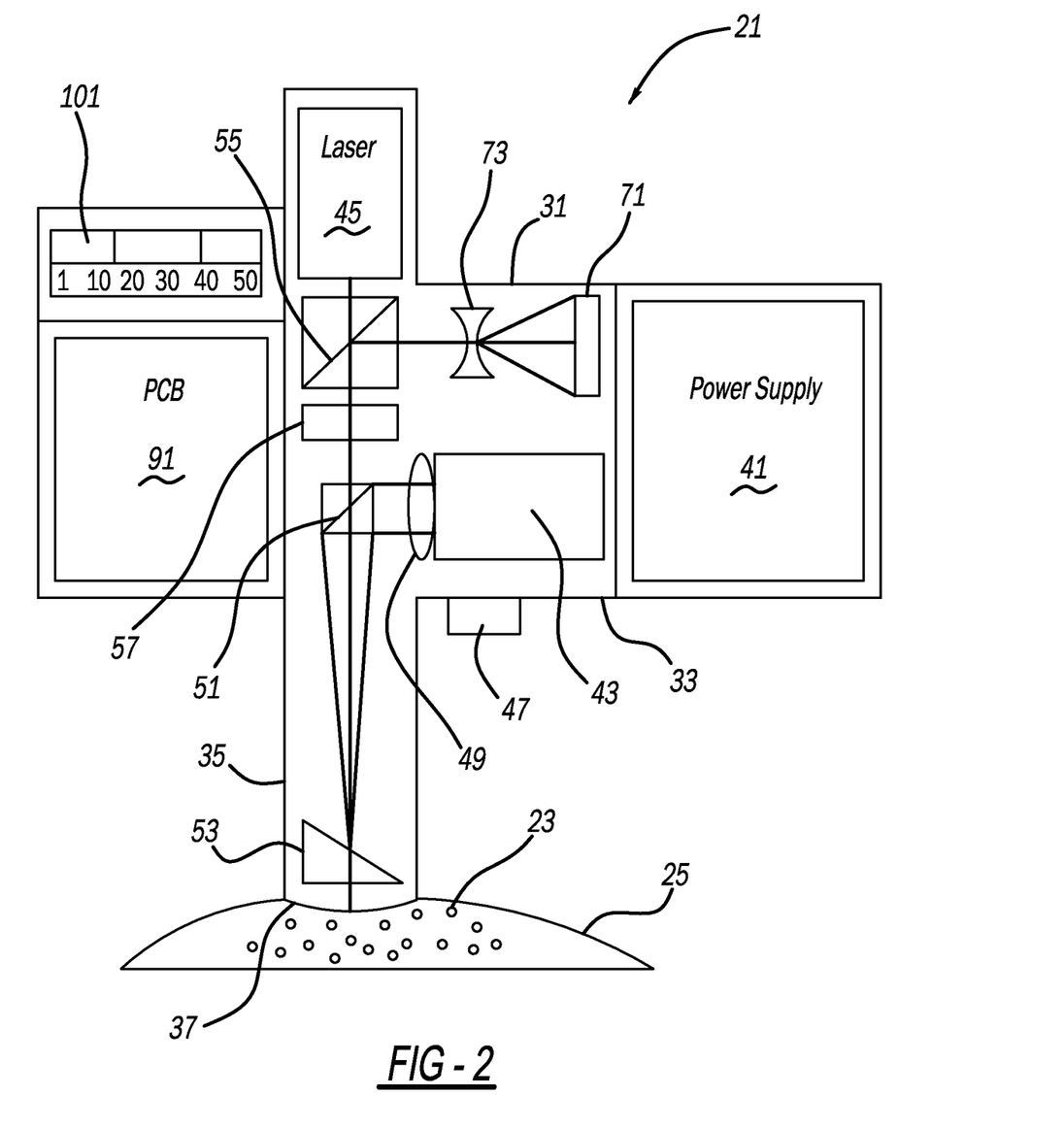
FIG. 2 is a diagrammatic side view showing the present laser system.
Figure 3:
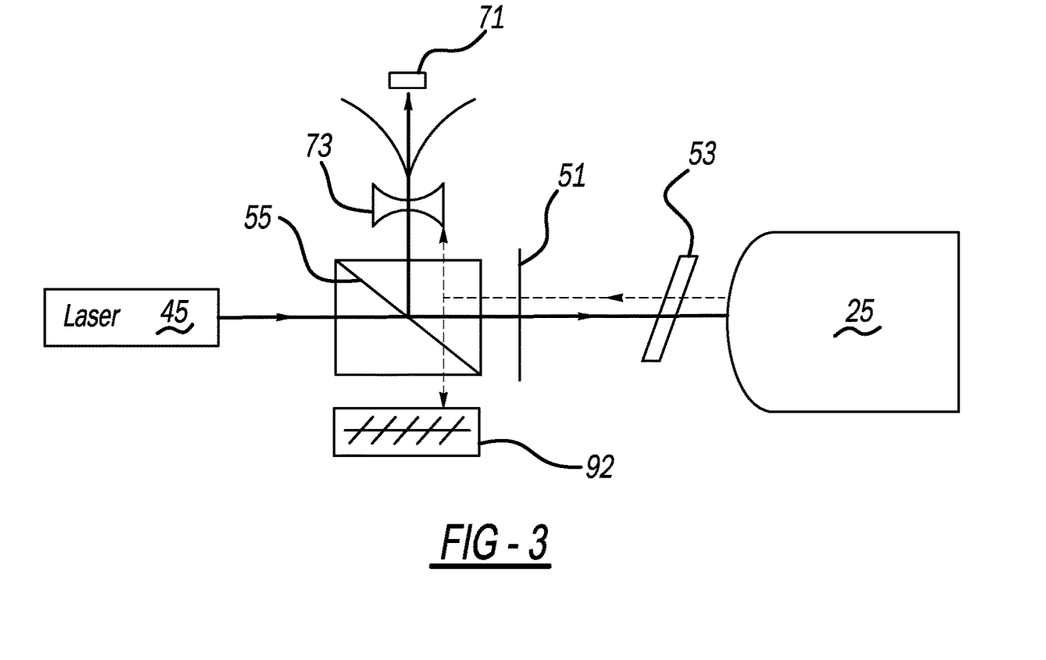
FIG. 3 is a diagrammatic view showing the present laser system.
Figure 4:
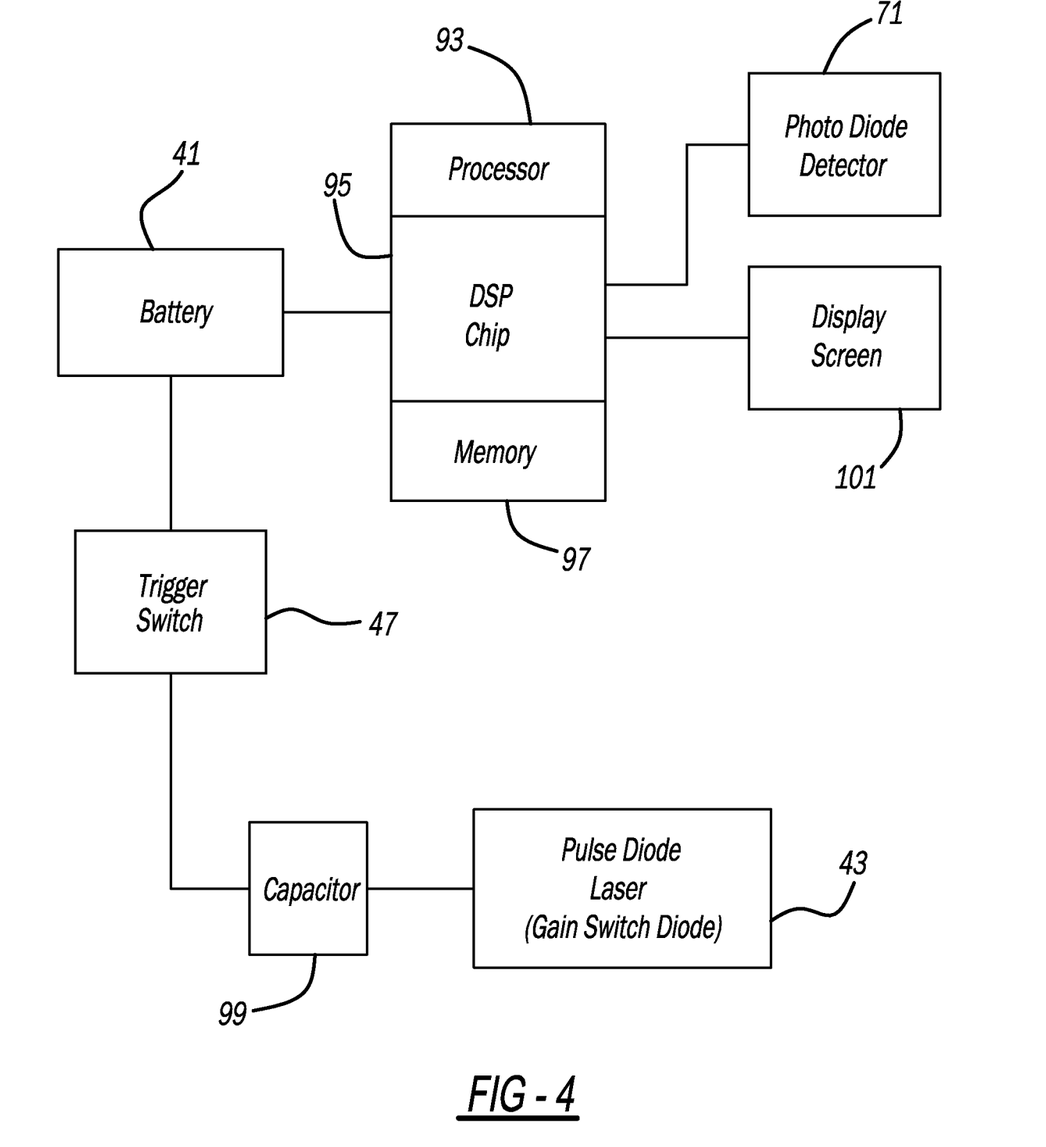
FIG. 4 is a circuit diagram for the present laser system.
Figure 5:
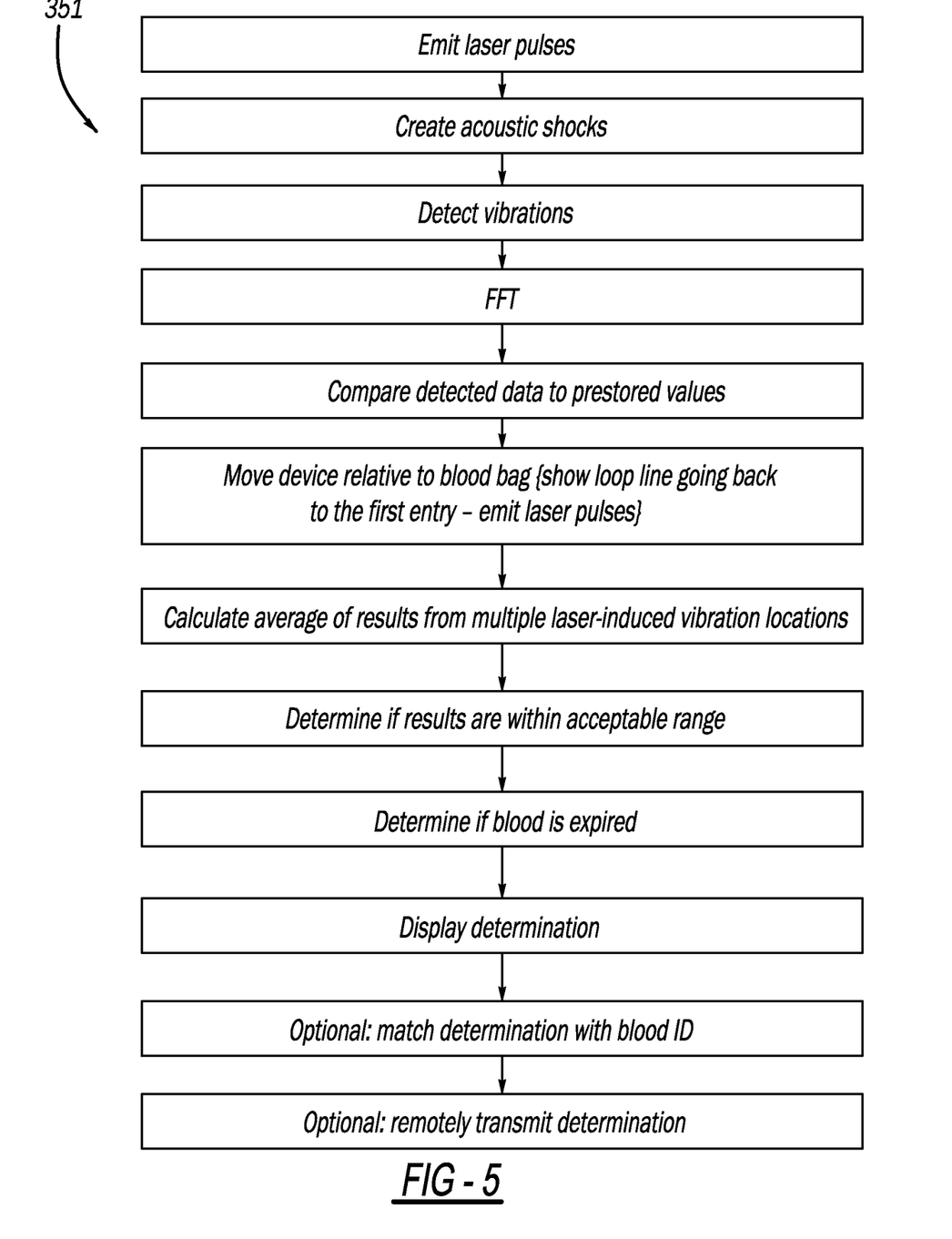
FIG. 5 is a software flowchart for the present laser system.

Reference should now be made to FIGS. 2 and 5, with regard to the operation of the present laser system. Laser 43 emits at least one light pulse upon red blood cells 23 within container 25 when in contact with housing 31. This burst of laser light energy is absorbed only by the blood cells and not the container bag and therefore induces a thermal shock or expansion of each of the adjacent red blood cells. The shock creates a mechanical vibration response that depends on the flexibility of the red blood cells elasticity. For example, healthy red blood cells have a soft membrane while older blood cell membranes are stiffer, which will cause different reflective acoustic signals that vary with the age or shelf life of the stored blood. Thus, the final acoustic response received by detector 71 contains characteristic information that is then used by computer software 351, stored in the non-transient read-only memory of chip 97, to automatically determine the health of red blood cells 23 in essentially real-time. The thermal shock is produced only by the red blood cells located nearest the surface of the storage bag 25 which thereby causes minimal degradation of all or most of the red blood cells. This method advantageously provides a non-invasive indicator of stored blood health without the use of imaging.

The digital processing chip converts the time data into a frequency-result spectrum that is used for analysis by the software instructions run programed on the microprocessor. The acquisition time takes approximately 1 microsecond which is at a speed fast enough to reduce motion artifacts. Multiple such spectra are acquired; for example, 10 spectra may take approximately 10 milliseconds to acquire when using a one kilohertz repetition rate laser, allowing rapid signal averaging by the software. The software compares the detected data to pre-stored values which have maximum and minimum limits to set an acceptable range based on prior blood experiments. It is envisioned that the user may move the laser system to various different positions along the same container, such as slowly moving it in a straight line from the top of the bag to the bottom of the bag, with repeating laser pulses during the movement to provide a sufficient statistical average of results, with at least three different locations providing a minimum for the averaging. The microprocessor controller and software then will determine if the actual detected results are within the acceptable range and based on this comparison calculation, the processor and software will determine if the blood is expired or not. The software and processor may additionally determine different actual shelf life grades of the blood ranging from A which is fresh and healthy, D for marginal, and F for unacceptable. These determination results are displayed on display screen 101 either in analog, digital, and/or graphical form.

The processor and programmed software instructions may optionally match the blood health determination with the identification of the blood, such as the blood type and/or source. Furthermore, the processor and software may optionally remotely transmit the determination results and the matching signals to a remote computer or database.

Figure 6:
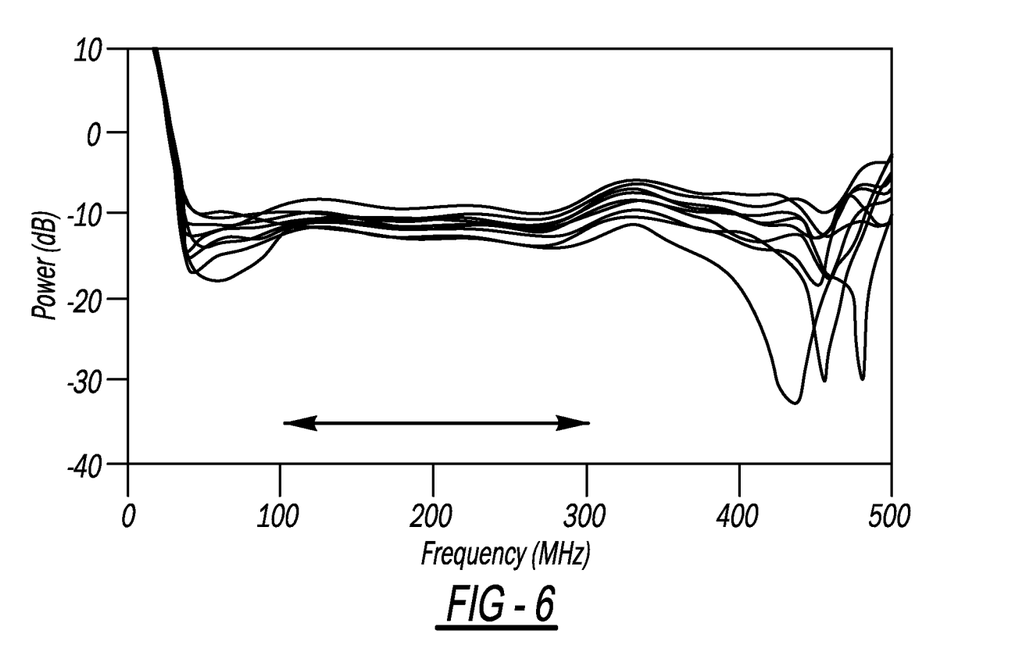
FIGS. 6 and 7 are graphs showing expected typical photoacoustic responses for red blood cell Rouleaux.
Figure 7:
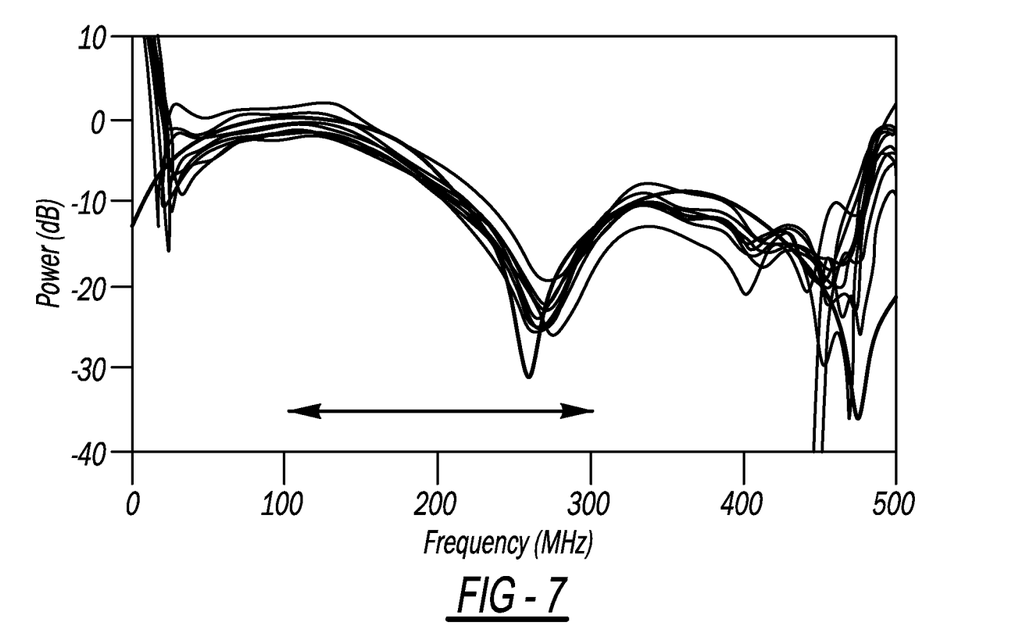

Finally, FIGS. 6 and 7 demonstrate the expected photoacoustic response from red blood cells based on power versus frequency. FIG. 6 graphically represents the power spectrum of a laser light from ten horizontal single red blood cells, while FIG. 7 graphically represents the laser light power spectrum of ten different red blood cells Rouleaux or aggregates. The graphs are created with an analytical cylindrical absorber model having a diameter of 7.8 µm and infinite length, and the double headed arrow in each indicates a transducer band width of 100-300 MHz.

The present laser system and method can alternately be used to assess various characteristics of human or animal tissue. For example, cancer causes the membranes of tissue cells to become stiffer than healthy cells. Thus, the present laser system and method can use non-imaging and non-invasive, optoacoustic detection of such tissue stiffness changes based on thermal shock of the cells caused by emitted laser light pulses employing the hardware and software discussed herein. This is ideally suited for determining the tissue characteristic for cells within 5 mm or less of the adjacent surface to which the portable housing contacts, and preferably less than or equal to 0.5 mm.

While various features of the present laser system have been disclosed, it will be appreciated that other variations can be employed. For example, the present laser system may automatically detect and determine that other characteristics are present in the stored blood such as bacteria or the like based on their optoacoustic vibrational signals. In another variation, the laser housing may be incorporated into a small table top, wheeled or fixed laser machine which is not intended to be hand held, although some of the advantageous of the preferred embodiment may not be fully realized. It is ultimately envisioned that other blood containers may be used such as rigid polymeric or glass boxes, or flexible tubes, although some of the present benefits may not be fully achieved. One or more of the features or components of one embodiment may be interchanged with or added to features and structures of any of the other embodiments, and all of the claims may multiply depend on each other in any order. The description of the invention is merely exemplary in nature and, thus, variations that do not depart from the gist of the invention are intended to fall within the spirit and scope of the present invention.

The invention claimed is:

1. A laser system comprising:
   (a) a container containing a biological tissue, the container being a flexible bag;
   (b) a laser operable to emit a laser beam at the container to vibrate the tissue;
   (c) a detector operable to detect a vibrational characteristic of the tissue as transmitted by the laser beam when it returns from the tissue;
   (d) a controller connected to the detector operable to automatically determine a characteristic of the tissue based at least in part on the vibrational characteristic detected by the detector, without the use of microscopy and without the use of imaging;
   (e) an electronic display operable to indicate a determination result from the controller;
   (f) a portable housing within which is mounted the laser, the detector and the controller, and the display being coupled to and moveable with the housing;
   (g) the controller using software to automatically determine health of cells of the tissue in essentially real-time, by the vibration which is due to an optoacoustic shock responsive to a membrane elasticity of the cells; and
   (h) the software automatically:
      averaging detected data taken at multiple locations of the container;
      comparing the detected data to pre-stored maximum and minimum limits; and
      causing the display to visually indicate the calculated determination results.

2. The system of claim 1, wherein the tissue is blood.

3. The system of claim 1, further comprising:
   a rechargeable power supply located within the housing;
   the housing including an elongated user-grippable handle and an elongated extension segment offset angled from an axis of the handle, a distal end of the extension segment contacting the container and the laser beam being emitted from the distal end of the extension segment and into the container; and
   the laser being located within the handle.

4. The system of claim 1, wherein:
   the laser is a diode laser emitting the laser beam at a wavelength greater than 400 nm and with a visible frequency between 450-600 nm;
   the laser beam includes coherent light; and
   the detector includes a photodiode which uses interferometry.

5. The system of claim 1, further comprising a second laser located within the housing.

6. The system of claim 1, further comprising an optic located in the housing that causes interference fringes on a sensed portion of the laser beam, motion of the fringes being sensed as the vibrational characteristic by the detector.

7. The system of claim 1, wherein the cells are blood cells and the container is a flexible polymeric bag.

8. A laser system comprising:
   (a) a container containing a biological tissue, the container being a flexible bag;
   (b) a laser operable to emit a laser beam at the container to vibrate the tissue;
   (c) a detector operable to detect a vibrational characteristic of the tissue as transmitted by the laser beam when it returns from the tissue;
   (d) a controller connected to the detector operable to automatically determine a characteristic of the tissue based at least in part on the vibrational characteristic detected by the detector, without the use of microscopy and without the use of imaging;
   (e) an electronic display operable to indicate a determination result from the controller;
   (f) a portable housing within which is mounted the laser, the detector and the controller, and the display being coupled to and moveable with the housing; and
   (g) wherein the housing includes a user-grippable handle and the detector is located within the handle, and the handle being elongated in a direction angularly offset from an emission direction of the laser beam from the housing to the container.

9. The system of claim 8, wherein the controller uses software which automatically:
   averages detected data taken at multiple locations of the container;
   compares the detected data to pre-stored maximum and minimum limits; and
   causes the display to visually indicate the calculated determination results.

10. The system of claim 8, wherein the software automatically determines cancer.

11. The system of claim 8, wherein the controller uses software configured to automatically determine health of blood cells of the tissue in essentially real-time, by the vibration which is due to an optoacoustic shock responsive to a membrane elasticity of the blood cells.

12. The system of claim 8, wherein the controller uses software configured to automatically determine a presence of a bacteria or virus.

13. A laser system comprising:
(a) a portable housing including a user-grippable handle;
(b) a laser, located within the housing, operable to emit a laser beam;
(c) a detector located within the housing; and
(d) a controller, located within the housing, including software which is configured to automatically determine health of blood by optoacoustic shock due to the laser beam interacting with a cell membrane of the blood, wherein the software is configured to automatically:
 (i) average detected data taken at multiple locations of a container holding the blood;
 (ii) compare the detected data to pre-stored maximum and minimum limits; and
 (iii) cause a display to visually indicate the calculated determination results.

14. The system of claim 13, further comprising:
at least a second laser, located within the housing, operable to emit a second laser beam; and
the detector using interferometry in combination with the laser beams.

15. The system of claim 13, wherein the software makes the blood health determination in an optical and nonintrusive manner without microscopy and without imaging.

16. The system of claim 13, wherein:
the container holding the blood is a flexible bag; and
the display is coupled to and movable with housing, the display operably providing a graphical user interface indicia representing the calculated determination results.

17. The system of claim 13, further comprising:
a rechargeable power supply located within the housing;
the user-grippable handle being elongated and the housing further comprising an elongated extension segment offset angled from an axis of the handle, a distal end of the extension segment contacting a container holding the blood, and the laser beam is emitted from the distal end of the extension segment and into the container; and
the laser being located within the handle.

18. The system of claim 13, further comprising an optic, located in the housing, that causes interference fringes on a sensed portion of the laser beam, motion of the fringes being sensed by the detector.

19. A method of using a laser comprising:
(a) contacting a specimen with a housing or a window coupled to the housing, the specimen being blood or a container containing the blood, the housing being a hand-held portable unit;
(b) creating a laser-induced vibrational or acoustic shock of the blood due to emission of a laser beam from the housing;
(c) using software in the housing to automatically determine expiration of the blood with assistance of step (b), without the use of microscopy and without the use of imaging; and
(d) visually displaying results of the determination.

20. The method of claim 19, wherein the container is a flexible bag which contains the blood.

21. The method of claim 19, wherein the software automatically determines a presence of a bacteria or virus.

22. The method of claim 19, further comprising moving the housing relative to the specimen, or vice versa, detecting multiple laser beam results at different locations of the specimen, using the software to average the results, and the visually displaying the results includes displaying the results via indicia coupled to and moveable with the housing.

23. The method of claim 19, wherein the laser beam has a wavelength greater than 400 nm and a pulse duration less than 100 ns, and the laser is moveable with the housing.

24. The method of claim 19, further comprising:
the container holding the blood being a flexible bag; and
moving a display with the housing, the display operably providing a graphical user interface indicia representing the visually displayed results.

25. The method of claim 19, further comprising:
recharging a power supply located within the housing;
gripping a handle, the housing further comprising an elongated extension segment offset angled from an axis of the handle, and the laser beam emitting from a distal end of the extension segment and into the container; and
the laser being located within the handle.

* * * * *